United States Patent [19]

Basava et al.

[11] Patent Number: 5,175,146
[45] Date of Patent: Dec. 29, 1992

[54] SYNTHETIC CALCITONIN PEPTIDES

[75] Inventors: Channa Basava, San Diego; Karl Y. Hostetler, Del Mar, both of Calif.

[73] Assignee: Vical, Inc., San Diego, Calif.

[21] Appl. No.: 572,674

[22] Filed: Aug. 24, 1990

Related U.S. Application Data

[63] Continuation-in-part of Ser. No. 446.932, Dec. 6, 1989, abandoned.

[51] Int. Cl.⁵ .................. A61K 37/02; A61K 37/30; C07K 5/00; C07K 7/00
[52] U.S. Cl. .................................. 514/12; 530/307; 530/324
[58] Field of Search .................. 530/307, 324; 514/12

[56] References Cited

U.S. PATENT DOCUMENTS

| | | | |
|---|---|---|---|
| 3,910,872 | 10/1975 | Riniker et al. | 530/307 |
| 4,397,780 | 8/1983 | Orlowski et al. | |
| 4,613,500 | 9/1986 | Suzuki et al. | |
| 4,622,386 | 11/1986 | Orlowski et al. | |
| 4,639,510 | 1/1987 | Orlowski | |
| 4,659,804 | 4/1987 | Orlowski et al. | |
| 4,663,309 | 5/1987 | Kaiser et al. | 530/307 |
| 4,758,550 | 7/1988 | Cardinaux et al. | |

FOREIGN PATENT DOCUMENTS 0297159  7/1987  European Pat. Off.

OTHER PUBLICATIONS

Channabasavaiah et al., *Biochem. Biophys. Res. Commun.*, 86, pp. 1266-1273 (1979).
Kaiser et al., *Science*, 223, pp. 249-255, 1984.
Kaiser, E. T. et al., *Anal. Biochem.* 34:595-598, (1969).
Kumar, M. et al., *J. Endocrinology* 33:469-475 (1964).
Liedtke, Clinical Chemistry, 27, 2025, 2028 (1981).
Lasmoles et al. *The EMBO Journal* 4(10):2603-2607 (1985).
Breimer, L. H., MacIntyre, I., and Zaidi, M., *Biochem. J.* 255:377 390 (1988).
Marx et al., *Science* 178:998-1001 (1972).
Epand et al., *Biochemistry* 25:1964-1968 (1988).
Habener et al., *Nature (London)* 232:91-92 (1971).
Pietta, P. G. and G. R. Marshall, *J. Chem. Soc. D*, 650-651 (1970).

Primary Examiner—Merrell C. Cashion, Jr.
Assistant Examiner—A. M. Davenport
Attorney, Agent, or Firm—Knobbe, Martens, Olson & Bear

[57] ABSTRACT

Synthetic hypocalcemic peptides which are similar in biological properties to native calcitonins as clinically useful agents. The peptides comprise analogues of native calcitonins having amino acid substitutions and deletions which act to improve potency, prolong duration of the hormonal effect, enhance receptor binding, and increase oral or nasal bioavailability. The calcitonin peptide analogues are less expensive and more easily synthesized than native calcitonins, and have improved resistance to inactivation or degradation. Methods are provided for the synthesis of these peptides.

Also, disclosed are novel cyclic peptides, including calcitonin, having increased stability with respect to proteolysis. Methods for the synthesis of these peptides are provided, comprising converting disulfide cyclic peptides and proteins to enzymatically and chemically stable cyclic peptide structures by the replacement of cysteine residues with dicarboxylic acids and diamino acids. The method is applicable to various naturally occurring peptides, their synthetic analogues or derivatives, and proteins.

13 Claims, No Drawings

SYNTHETIC CALCITONIN PEPTIDES

This application is a continuation-in-part of application Ser. No. 07/446,932, filed Dec. 6, 1989 and now abandoned.

BACKGROUND OF THE INVENTION

This invention relates to synthetic peptides having hypocalcemic action similar to that of natural calcitonins of various species. It relates specifically to synthetic calcitonin peptides having a hypocalcemic potency greater than that of human calcitonin and/or having less immunogenicity in humans than calcitonins from foreign species. The invention also relates to synthetic analogues of calcitonin as well as other naturally occurring bioactive peptides having a cyclic peptide structure, wherein the synthetic cyclic strucutre has improved resistance to metabolic attack. It relates as well to processes for producing these synthetic peptides.

Calcitonins are 32-amino acid peptide hormones invovled in the regulation of calcium metabolism. Calcitonin participates with parathyroid hormone in the regulation of bone metabolism and the homeostatic regulation of blood calcium levels according to mechanisms that are not completely understood. Normal bone metabolism comprises a balance of osteolytic resorption and osteoblastic formation of new bone to fill the resorption spaces. Calcitonin appears to oppose the osteolytic activity of parathyroid hormone, acting directly to inhibit bone resorption by altering osteoclastic and osteocytic activity. Calcitonin may also enhance new bone formation by stimulation of osteoblasts.

Bone resorption causes a release of clacium and alkaline phosphatase into the circulation, and the appearance of urinary hydroxyproline, resulting from the breakdown of collagen-contining bone matrix. According to physiological mechanisms, elevated serum calcium levels promote the secretion of calcitonin, which has a hypocalcemic effect. In normal individuals, bone resorption is minimal, and exogenous calcitonin has no hypocalcemic effect.

Many diseases in man, including not only those associated with bone resorption, but those related to other disorders, including malignancy, are marked by hypercalcemia, the persistence of which can be life-threatening. Exogenous calcitonin has proved to be a valuable therapeutic agent in treating these disorders. Calcitonin therapy is thus effective in diminishing hypercalcemia in patients with hyperparathyroidism, idiopathic hypercalcemia of infancy, Vitamin D intoxication, and osteolytic bone metastases. It similarly diminishes the hypercalcemia that accompanies malignancies with or without metastasis, and that of multiple myeloma.

Calcitonin is also effective in treating disorders wherein bone turnover or resorption is accelerated, but changes in serum calcium levels are not detected. One important disease of this type is osteoporosis, particularly postmenopausal type, wherein there is a progressive loss of bone mass. The efficacy of calcitonin in osteoporosis is determined by its ability to increase total body calcium. Paget's disease (osteitis deformans) is a disorder characterized by excessive resorption of bone accompanied by the imbalanced formation of new (pagetic) bone which lacks the characteristic architecture of normal bone. Calcitonin reduces the elevated serum levels of alkaline phosphatase and urinary hydroxyproline seen in individuals with this disease. Benefits of calcitonin therapy in Paget's disease are indicated by radiologic evidence of bone remodeling, correlated with a reduced number of osteoclasts seen in bone biopsies, consistent with a decrease in bone resorption. Calcitonin also provides relief from the pain and tenderness associated with the disease.

Calcitonins are found in a variety of vertebrate species including mammals, birds and fish. The hormone is secreted by the C cells, which are localized in the thyroid gland of mammals, and in the ultimobranchial glands in the lower vertebrates.

Human calcitonin (hCT) has the following amino acid sequence:

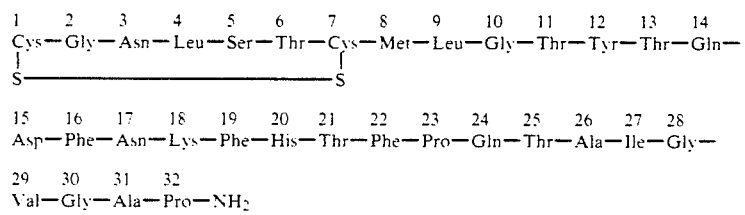

Calcitonin shows considerable divergence in amino acid sequence between lower vertebrates and higher vertebrates. However, highly conserved residues are clustered at the two ends of the calcitonin molecule believed to be important for biological activity. For example, a 1-7 disulfide bridge and a C-terminal proline amide are invariate among all species. Several other invariate amino acid residues occur at the N-and C-terminal ends. The middle portion of the molecule, positions 10 to 27, which is thought to control the potency and duration of the peptide, is quite variable in amino acid composition. Breimer, L. H., MacIntyre, I., and Zaidi, M., *Biochem. J.* 255:377∝390 (1988) have reviewed the structures and biological properties of calcitonin peptides from various species and this information is hereby incorporated by reference.

Calcitonins of certain non-human species appear to be more potent in humans than human calcitonin. Calcitonins that are ultimobranchial in origin, such as salmon, eel, and avian are more potent than thyroidal calcitonins, such as human or porcine hormones. Salmon, eel, porcine and human calcitonins are currently in clinical use for the treatment of Paget's disease, osteoporosis and the hypercalcemia of malignancy.

The correlation of potency with the structure of the calcitonin peptides is not well understood. Improved potency may be due to an amino acid sequence which permits a peptide conformation that is more favorably bound to the hormone receptor (Marx et al., *Science* 178:998-1001 (1972). A conformation that is more flexible, a feature provided by smaller less bulky amino acids, has been determined to affect biological activity (Epand et al., *Biochemistry* 25:1964-1968(1988)). The identical biological potencies of eel and salmon calcitonin may accordingly be explained on the basis of similar primary structures and similar flexibility.

An alternative basis for the relatively greater potency of non-human calcitonins may be that the amino acid sequences of these calcitonins, characteristic of particular species, offers greater resistance to metabolic degradation in the human body than human calcitonin, and for this reason has a more persistent effect (Habener et al., *Nature(London)* 232:91–92 (1971)). For example, salmon calcitonin remains potent for about six hours after administration, while human calcitonin remains potent for about two hours.

In spite of their higher potency, however, the calcitonins from other species, such as the ultimobranchial calcitonins, are not entirely satisfactory for human clinical use, primarily because the variable, poorly conserved middle portion of non-human calcitonins acts as an immunogen in vivo. The resulting antibody production can therefore limit their usefulness.

After administration to man by subcutaneous injection, all the natural calcitonins have a relatively short half life because, in spite of species differences which act to retard proteolysis by plasma enzymes, they are subject to rapid renal and tissue clearance as well. Also, because the activity of natural calcitonins depends on an intact disulfide bond between the cysteine groups at positions 1 and 7, the reduction of this unstable bond in vivo rapidly converts biologically active peptides to an inactive form.

It would be useful to have calcitonin peptides which are more effective in clinical use either because of greater stability in vivo, and/or higher potency and longer duration of action than the native hormones. It would also be useful to have calcitonin peptides which are less immunogenic than the native hormones.

It would also be useful to have calcitonin peptides which are convenient and inexpensive to synthesize and that can be stored for a period of time prior to clinical use.

Furthermore, analogues with increased lipophilicity and hydrophobicity could have altered pharmacokinetics and possess improved parenteral, nasal or oral bioavailability. It would, further, be advantageous to extend these advantages to other bioactive peptides tive cyclic peptides having i-ncreased chemical and enzymatic stability.

It is also an object of the invention to provide synthetic cyclic peptides which are inexpensive to manufacture and which are stable under conventional storage conditions.

It is also an object of the invention to provide methods for the synthesis of these cyclic peptides.

SUMMARY OF THE INVENTION

According to one aspect of the invention there are provided synthetic peptides that are analogues of calcitonin peptides, possessing hypocalcemic calcitonin activity and having the formula $$Y\text{-}(R1\text{-}R2\text{-}A1\text{-}A2\text{-}A3\text{-}A4\text{-}Ser\text{-}Thr)_m\text{-}A7\text{-}xCT(8\text{-}32) \quad \text{(I)}$$

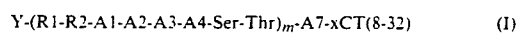

wherein Y, R1, R2, A1, A2, A3, A4, A7, and xCT are as defined herein, and pharmaceutically acceptable salts thereof.

In one embodiment of this aspect of the invention, at least one of the amino acid residues at positions 8, 12, 16, 21, or 27 of a vertebrate calcitonin is replaced by leucine. Leucine can also be attached at position 0. Preferred peptides of this group are (Leu-8)-xCT; (Leu-8,12)-hCT; Leu-8,12,16)-hCT; (Leu-8,12,16,27)-hCT; Leu(Leu-8)-xCT; Leu(Leu 8,12)-hCT; and Leu(Leu-8,12,16)-hCT.

Another embodiment comprises analogues of calcitonin peptides having deletions of at least one amino acid residue at positions 19-22. Preferred peptides of this group are des(22)-xCT(8-32); des(19-22)-xCT(8-32); ((CHX-Ser)-5, Ala-7, des(22))-xCT (5-32); ((CHX-Ser)-5, Ala-7, des(19-22))-xCT(5-32); ((12-Aminododecanoyl-Ser)-5, Ala-7, des(22))-xCT(5-32); and ((12-Aminododecanoyl-Ser)-5, Ala-7, des(19-22))-xCT(5-32).

According to other embodiments of this aspect of the invention, there are provided analogues of calcitonin peptides wherein the disulfide bridge between cysteine residues at positions 1 and 7 is replaced by other cyclizing structures. In one of these embodiments, A1 and A7 are different and are either a dicarboxylic acid or a diamino acid and are linked through an amide bond. Preferred peptides of this group are

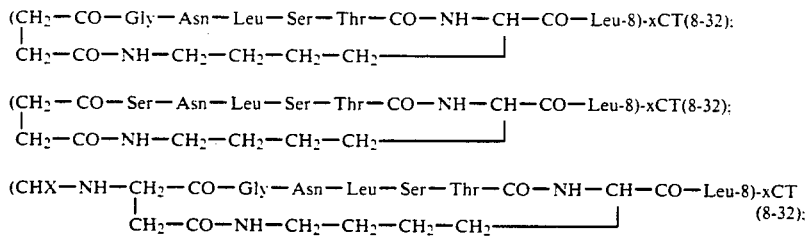

and

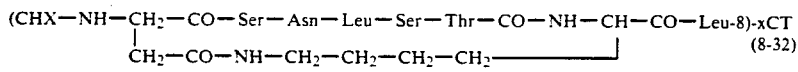

having structural similarities to calcitonin.

Accordingly, it is an object of the invention to provide synthetic calcitonin peptides which are safer and more effective in the treatment of human disease than native calcitonins from human and other species.

It is also an object of the invention to provide synthetic analogues of calcitonin peptides and other bioac- Another embodiment according to this aspect of the invention comprises analogues of calcitonin peptides wherein A7 is lysine. In one such embodiment, there are provided branched chain peptides, wherein m is 2 and identical peptide sequences are attached to the A7 lysine. Preferred among peptides of this group are ((Leu-Ala-Ala-Ser-Leu-Ser-Thr-)$_2$-Lys$^7$)cCT; ((Leu-Ala-Gly-Asn-Leu-Ser-Thr)$_2$-Lys-7)-xCT (7-32); ((Leu-Ala-Ser-Asn-Leu-Ser-Thr)$_2$-Lys-7)-xCT (7-32); ((N-Acetyl-aminooctanoyl-Ser-Thr)$_2$-Lys-7)-xCT (7-32); ((Ser-Thr)$_2$-Lys-7)-xCT (7-32); ((Chx-Ser-Thr)$_2$-Lys$^7$)-xCT; ((Leu-Ala-Ala-Ser-Leu-Ser-Thr)$_2$-Lys-7, Leu-8)-cCT(8-32); ((Leu-Ala-Gly-Asn-Leu-Ser-Thr)$_2$-Lys-7, Leu-8)-xCT(8-32); ((Leu-Ala-Ser-Asn-Leu-Ser-Thr)$_2$-Lys-7, Leu-8)-hCT(8-32); ((Leu-Ala-Ser-Asn-Leu-Ser-Thr)$_2$-Lys-7, Leu-8,12)-hCT(8-32); ((Leu-Ala-Ser-Asn-Leu-Ser-Thr)$_2$-Lys-7, Leu-8,12,16)-hCT(8-32); and ((Chx-Ser-Thr)$_2$-Lys-7, Leu-8)-xCT.

In a related embodiment of calcitonin analogues wherein A7 is lysine, Y1 is a dicarboxylic acid and identical peptide sequences, branched from lysine, are attached at the dicarboxylic acid to form a cyclic structure. Preferred peptides of this group are thesized. The method can further comprise the step of contacting the synthesized branched calcitonin peptide with succinic anhydride in a suitable solvent whereby the amino groups of the terminal residues of said calcitonin peptide are coupled to the carboxyl groups of a succinic acid molecule to form a cyclic structure.

The invention further provides methods for treating disease, comprising the use of the novel calcitonin analogues described. A method provided for treating hypercalcemia comprises the steps of administering to said mammal in need of such treatment an effective, blood calcium-reducing amount of a synthetic calcitonin peptide of the invention. A method provided for treating Paget's disease or osteoporosis comprises administering to an affected subject a bone resorption-opposing amount of a calcitonin analogue of the invention for a period sufficient to reduce or eliminate the resorption of bone.

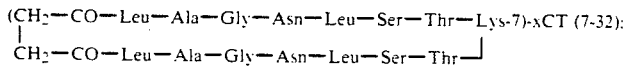

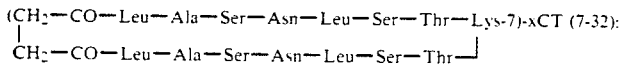

and

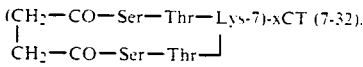

Also according to this aspect of the invention, there are provided analogues of the calcitonin peptide of the human β gene sequence wherein leucine is substituted at the 21 position.

According to another aspect of the invention there are provided methods for synthesizing the novel peptides of the invention. A method for preparing a branched chain peptide having the general formula (R-1 to R-6)2-Lys-7)-xCT, comprises the steps of coupling an amino group of a first amino acid with a carboxyl group of a second amino acid to form a dipeptide; repeating the coupling with successive amino acids to obtain a selected vertebrate calcitonin peptide sequence in which a lysine residue occupies position 7; coupling both the alpha and epsilon amino groups of the lysine residue with the carboxyl groups of R6 residues; and repeating the coupling of amino acids to the peptide sequence until the complete indicated sequence is syn- According to another aspect of the invention, there are provided analogues of disulfide cyclic peptides, comprising bioactive peptides in addition to calcitonin, wherein members of a cysteine residue pair of the cyclic peptide that form the disulfide bond are replaced by residues having available functional groups capable of forming an amide bond with each other. A preferred embodiment comprises analogues wherein one of the cysteine groups of the disulfide cyclic peptide is replaced by a diamino acid and another is replaced by a dicarboxylic acid. In a particularly preferred embodiment, the diamino acid is lysine or ornithine. Preferred cyclic peptides wherein the disulfide linkage is thus replaced are:

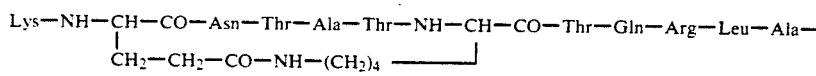

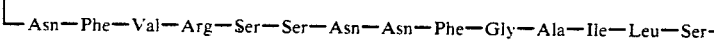

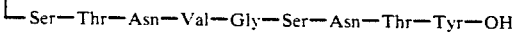

or the corresponding amide;

(b) a cyclic analogue of luteinizing hormone releasing hormone (LHRH) agonist ((D-beta-Naphthylalanine)$^6$-LHRH, having the structure

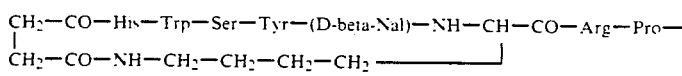

—Gly—NH$_2$;

(c) a cyclic analogue of the luteinizing hormone releasing hormone (LHRH) antagonist ((D-Phe)$^2$, (D-beta-Naphthylalanine)$^6$-LHRH, having the strucutre

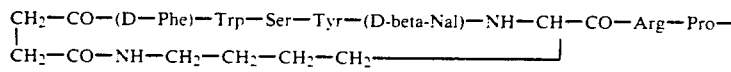

—Gly—NH$_2$;

(d) a cyclic analogue of the diuretic hormone vasopressin, having the structure

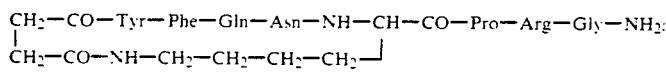

(e) a cyclic analogue of the peptide hormone oxytocin, having the structure

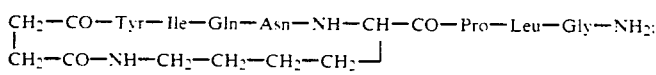

(f) a cyclic analogue of somatostatin, having the structure

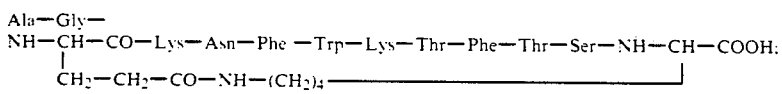

(g) a novel cyclic analog of human atrial natriuretic peptide, having the structure

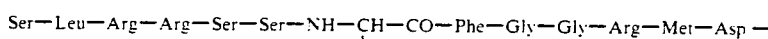

—Phe—Arg—Tyr—OH; and (h) a novel analogue of human calcitonin gene related peptide, having the structure

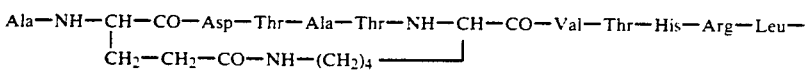

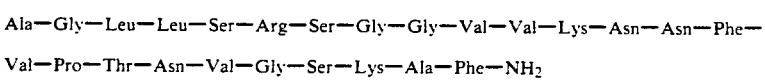

Val—Pro—Thr—Asn—Val—Gly—Ser—Lys—Ala—Phe—NH$_2$

According to yet another aspect of the invention there are provided methods of synthesizing a cyclic peptide by stepwise chain elongation on a polymeric support, comprising the steps of incorporating a diaminocarboxylic acid into a selected position in a peptide chain during peptide synthesis, said diaminocarboxylic acid having different protecting groups on the alpha amino group and the side chain amino group; selectively removing the protecting group from either the alpha amino group or the side chain amino group of said diaminocarboxylic acid; continuing synthesis by incorporating from 1-50 additional amino acids consecutively into the peptide chain ending with a terminal amino acid having a protected alpha amino group; selectively removing the remaining protecting group from either the alpha amino group or the side chain amino group of said diaminocarboxylic acid; coupling to the deprotected group an amino dicarboxylic acid, said amino dicarboxylic acid having the alpha carboxyl group protected; and deprotecting the alpha amino group of said terminal amino acid and the alpha carboxyl group of said amino dicarboxylic acid and linking said groups. There is further provided a method for synthesizing a cyclic peptide by stepwise chain elongation on a polymeric support, comprising the steps of incorporating an aminodicarboxylic acid into a selected position in a peptide chain during peptide synthesis, said aminodicarboxylic acid having a protecting group on the side chain carboxyl group; continuing synthesis by incorporating from 1-50 additional amino acids consecutively into the peptide chain ending with a diamino acid, said diamino acid having a protected side chain amino group; and removing the side chain protecting groups from said amino dicarboxylic acid and said diamino acid and linking said groups.

In preferred embodiments of the method the diaminocarboxylic acid is lysine-or ornithine, and the amino dicarboxylic acid is aspartic acid or glutamic acid. The method described can comprise the additional step of introducing at least one additional amino acid to the peptide chain.

According to yet another aspect of the invention there are provided cyclic peptides produced by any one of the methods disclosed herein. Also provided are biologically active fragments of any one of the peptides described, preferably those generated by the action of endogenous proteases on those peptides.

DETAILED DESCRIPTION OF THE INVENTION

The present invention relates in one aspect to analogues of hypocalcemic peptides, their pharmaceutically acceptable salt forms or compositions thereof, processes for their preparation, and their use in regulating serum calcium levels of mammals.

The invention in a related aspect is directed to analogues of bioactive cyclic peptides, for which calcitonin is the paradigm, having increased stability with respect to chemical and enzymatic proteolysis.

We have synthesized hypocalcemic peptides that are analogues of native calcitonins but in which amino acid residues are substituted or deleted so as to provide a more potent biological response and/or to reduce the immunogenic activity normally experienced with the use of native calcitonins of non-human species. The amino acid sequence of the peptides has been selected according to principles of biological activity to provide hypocalcemic agents having increased potency, a longer duration of action, enhanced receptor binding properties, increased stability to enzyme degradation and increased nasal or oral bio-availability.

It has been suggested that conformational flexibility of a calcitonin peptide can enhance its biological effectiveness (Epand, R. M., et al. *Biochemistry* 25:1964-1968 (1986)). Flexibility has been shown to be improved where bulky residues, which promote the formation of rigid helices, are absent (Kaiser, E. T. and Kedzi, F. J., *Science* 223:249-255 (1984)).

The calcitonin analogues of the invention therefore include hypocalcemic peptides, corresponding in part to native calcitonins, but in which flexibility has been improved by the elimination of certain amino acid residues. Some of the analogues have up to eight amino acids missing from the natural sequence. For example, the amino acid sequence comprising residues 19-22 is shown to be non-essential for biological activity; therefore one group of analogues according to the invention comprises hypocalcemic peptides in which at least one and as many as all of these residues of native calcitonin have been eliminated.

In a second group of analogues, the flexibility of the peptide chain is increased by replacement of some amino acid residues by a variety of less bulky moieties. Amino acid residues of calcitonin at positions 8, 12, 16, and 27 of calcitonin have been replaced in the analogues of the invention by leucine substitution. For the predicted calcitonin sequence from the human β gene (Breimer, L. H. et al. *Biochemistry* 255:377-390 (1988), the methionine residue at position 21 has been replaced by leucine.

Calcitonin analogues having increased stability to in vivo metabolic processes have been synthesized by replacing or eliminating labile bonds.

The cyclic structure based on cysteine disulfide bonding between residues at positions 1 and 7 appears to be essential to biological activity; however, this structure is labile in vivo to metabolic events which open the bond. Therefore, in some of the calcitonin peptides of this invention we have replaced the disulfide bridge with ring structures having greater stability. For example, cyclic structures have been prepared by linking the N-terminal amino group of the peptide and the epsilon amino group of a lysine residue at position 7 through a dicarboxylic acid. Alternatively, replicate amino acid sequences are attached to the alpha and epsilon amino groups of lysine at position 7 and the terminal amino groups of these sequences are then linked through a dicarboxylic acid. Both these types of ring structures are expected to be more stable than the disulfide bridge present in the natural calcitonins.

With the objective of providing calcitonin peptides that are economical to prepare and lack the labile disulfide bridge, we have designed and synthesized a number of linear peptides. They are obtained by replacing the cysteine residues at positions 1 and 7 with amino acids such as alanine or glycine. These linear calcitonin peptides are easier to prepare and purify, and are more stable than peptides containing the disulfide bridge.

Another group of calcitonin peptides of the invention possess branched structures prepared by coupling replicate peptides to both alpha and epsilon amino groups of a lysine residue at position 7. These peptides could offer multiple binding sites to the hormone receptor and are expected to possess increased potency and longer duration of action.

Since metabolic degradation occurs in the soluble phase of cells, we have constructed calcitonin analogues having increased hydrophobicity so as to resist or retard the process. The hydrophobicity has been provided by attaching various alkyl, aryl, or heterocyclic groups at the N-terminal end of the peptides. Preferred examples are those calcitonin analogues comprising 12-aminododecanoyl-Ser-5 at the N-terminal end.

The synthetic hypocalcemic peptides of the invention therefore have the formula:

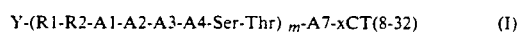

wherein
Y is a dicarboxylic acid selected from the group consisting of succinic acid, glutaric acid, L-aspartic acid, D-aspartic acid, L-glutamic acid, D-glutamic acid, or no moiety;
R1 is H, H-(CH$_2$)$_n$—CO—, H2N—(CH2)n—CO—, or Z—CO—(CH2)n—CO—(wherein Z is HO—, cholesterol, adamantyl alcohol, or an aromatic alcohol), L-threonine or D-threonine, L-alanine, D-alanine, L-leucine, D-leucine, cyclopropane carboxyl (CPRC), cyclopentane carboxyl (CPC) cyclohexane carboxyl (CHC), cyclohexylpropionyl (CHX), cycloheptane carboxyl (CHPT), adamantaneacetyl (ADM), adamantane carboxyl (ADC), or acyl groups of aromatic or heterocyclic carboxylic acids;

R2 is 1-amino-1-cyclopropane carboxyl (ACPR), 1-amino-1-cyclopentane carboxyl (ACPC), 1-amino-1-cyclohexane carboxyl (ACHC) 1-amino-1-cycloheptane carboxyl (ACHP), no moiety, or is the same as R1;

A1 and A7 are the same or different and are independently L-cysteine, L-threonine, D-threonine, L-tyrosine, D-tyrosine, L-alanine, D-alanine, L-leucine, D-leucine, or 2-aminoisobutyric acid; or A1 and A7 are different and A1 is mercaptopropionic acid, mercaptoacetic acid, H—(CH$_2$)n—CO—, 1-amino-1-cyclopropane carboxyl, 1-amino-1-cyclopentane carboxyl, 1-amino-1-cyclohexane carboxyl, 1-amino-1-cycloheptane carboxyl, or no moiety; or A1 and A7 are different and are either a diamino acid or dicarboxylic acid selected from the group consisting of succinic acid, glutaric acid, L-aspartic acid, D-aspartic acid, L-glutamic acid, and D-glutamic acid, except that A7 is not succinic acid;

A2 is glycine, L-alanine, L-serine, or no moiety;

A3 is L-asparagine, L-serine, or no moiety;

A4 is L-leucine or no moiety;

m is 1 or 2;

n is 1 to 22;

wherein xCT is an amino acid sequence corresponding at least at residues 9–11, 13–15, 17, 18, 23–26, and 28–32 to murine, salmon, eel, avian, porcine, bovine, ovine, or human calcitonin, provided that when the sequence (R1-R2-A1-A2-A3A4-Ser-Thr)$_m$-A7 is identical to the corresponding sequence of a natural calcitonin of a species, xCT(8-32) is not identical to the corresponding sequence of said calcitonin;

or pharmaceutically acceptable salts thereof;

with the proviso that if A1 and A7 are the same and are alanine, R2 is present and is not H.

Amino acids discussed herein are of the L-form unless otherwise mentioned; abbreviations used are those commonly employed in the peptide art and described in the literature, eg. IUPAC-IUB Commission on Biochemical Nomenclature, *J. Biol. Chem.* 247, 979–982 (1972). Human calcitonin comprises the presently known human calcitonin sequence as well as the sequence predicted from the DNA sequence of the human β gene (Briemer, L. H., et al. *Biochem. J.* 255:377–390 (1988) in which two of the invariant residues (positions 1 and 9) are altered and are: Tyr-1, Gln-9.

((Leu—Ala—Ala—Ser—Leu—Ser—Thr)$_2$—Lys-7, Leu-8)-cCT(8-32);

((Leu—Ala—Gly—Asn—Leu—Ser—Thr)$_2$—Lys-7, Leu-8)-xCT(8-32);

((Leu—Ala—Ser—Asn—Leu—Ser—Thr)$_2$—Lys-7, Leu-8)-hCT(8-32);

((Leu—Ala—Ser—Asn—Leu—Ser—Thr)$_2$—Lys-7, Leu-8,12-hCT(8-32);

((Leu—Ala—Ser—Asn—Leu—Ser—Thr)$_2$—Lys-7, Leu-8,12,16-hCT(8-32);

((Chx—Ser—Thr)$_2$—Lys-7, Leu-8)-xCT;

((Leu—Ala—Gly—Asn—Leu—Ser—Thr)$_2$—Lys-7)-hCT(7-32);

((Leu—Ala—Ser—Asn—Leu—Ser—Thr)$_2$—Lys-7)-xCT(7-32);

((Leu—Ala—Ala—Ser—Leu—Ser—Thr)$_2$—Lys-7)-cCT;

((N-Acetyl-aminooctanoyl-Ser—Thr)$_2$—Lys-7)-xCT(7-32);

((Ser—Thr)$_2$—Lys-7)-xCT(7-32);

((Chx—Ser—Thr)$_2$—Lys-7)-xCT(7-32);

```
((CH2—CO—Gly—Asn—Leu—Ser—Thr—CO—NH—CH—CO—Leu-8-hCT(8-32);
  |
  CH2—CO—NH—CH2—CH2—CH2—CH2——————|

(CH2—CO—Leu—Ala—Gly—Asn—Leu—Ser—Thr—Lys-7-hCT(7-32);
 |
 CH2—CO—Leu—Ala—Gly—Asn—Leu—Ser—Thr —|

(CH2—CO—Leu—Ala—Ser—Asn—Leu—Ser—Thr—Lys-7)-xCT(7-32);
 |
 CH2—CO—Leu—Ala—Ser—Asn—Leu—Ser—Thr —|

(CH2—CO—Ser—Thr—Lys-7)-xCT(7-32);
 |
 CH2—CO—Ser—Thr —|

(CH2—CO—Ser—Asn—Leu—Ser—Thr—CO—NH—CH—CO—Leu-8)-xCT(8-32);
  |
  CH2—CO—NH—CH2—CH2—CH2—CH2 —|

(CHX—NH—CH2—CO—Gly—Asn—Leu—Ser—Thr—CO—NH—CH—CO—Leu-8)-hCT(8-32)
    |
    CH2—CO—NH—CH2—CH2—CH2—CH2———|
```

-continued

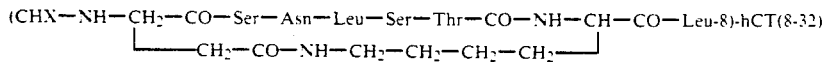

((CHX—Ser)-5, Ala-7, des(22))-xCT(5-32);

((CHX—Ser)-5, Ala-7, des(19-20))-xCT(5-32);

((12-Aminododecanoyl-Ser)-5, Ala-7, des(22))-xCT(5-32);

((12-Aminododecanoyl-Ser)-5, Ala-7, des(19-22))-xCT(5-32);

((12-aminododecanoyl- Ser)-5, Ala-7)-xCT(5-32);

((12-Aminododecanoyl-Ser)-5, Ala-7, Leu 8,12)-hCT(5-32);

((12-Aminododecanoyl-Ser)-5, Ala-7, Leu 8,12,16)-hCT(5-32);

((D-Ala-12-aminododecanoyl-Ser)-5, Ala-7)-xCT(5-32);

D-Ala-(Leu-8,12,16)-hCT;  Leu-(Leu-8)-hCT;  Leu-(Leu 8,12)-hCT;

Leu-(Leu-8,12,16)-hCT;  (Leu-8,12,16,27)-hCT;

Leu(Leu-8)-xCT;  Leu(Leu-8,27)-xCT;

(Leu-8)-hCT;  (Leu-8,12)-hCT;  (Leu-8,12,16)-hCT;

(Leu-8)-xCT;  and  (Leu-8,27)-xCT.

wherein h represents human, and x represents human or murine or salmon or eel or avian or porcine or bovine or ovine; and analogs of human calcitonin peptide from the β gene, having the strucutre

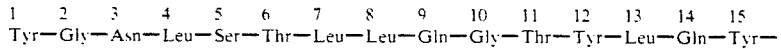
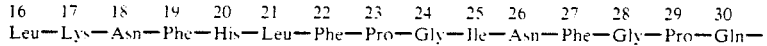
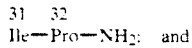

and

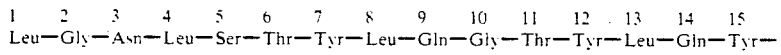
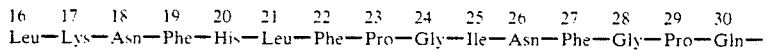
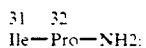

Peptides containing basic amino acids such as lysine, arginine, and histidine may exist in the form of salts such as chloride, acetate, phosphate, citrate, succinate, oxalate, etc. Acetate and hydrochloride salt forms are particularly preferred. For the purposes of this invention, peptides of the Formula I and their acid addition salts are considered to be one and the same.

Peptide Synthesis

The peptides of the invention may be synthesized by solid phase peptide synthesis (SPPS) procedures known to those skilled in the art and described in detail in the literature; eg. Barany, G. and R. B. Merrifield, in *The Peptides*, Vol. 2; E. Gross & J. Meienhoffer, eds.; Academic Press, New York, pp 3-284 (1979). Synthesis of peptides such as calcitonin which contain a C-terminal amide group is preferably carried out on a 4-methylbenzhydrylamine-divinylbenzene-copolystyrene, referred to as MBHA resin which is commercially available from supply houses. Its preparation and application in SPPS are well documented in the field, see Pietta, P. G. and G. R. Marshall, *J. Chem. Soc. D*, 650-651 (1970), and Channabasavaiah, K. & J. M. Stewart, *Biochem. Biophys. Res. Commun.* 86, 1266-1273, (1979).

Peptides described in this invention are prepared starting from t-butyloxycarbonyl-proline linked to MBHA resin (Boc-Pro-MBHA) which is also commercially available. Boc-Pro-MBHA resin is treated with anhydrous trifluoroacetic acid (TFA) or 25% to 75% mixture of TFA in dichloromethane (TFA-DCM) to deprotect the amino group, and the resulting salt neutralized using 5% to 20% triethylamine in DCM (TEA-DCM) or 5% to 20% diisoproylethylamine in DCM (DIEA-DCM) to furnish H₂N-Pro-MBHA resin.

The next amino acid in the sequence (AA31) containing appropriate protecting groups is coupled to H₂N-Pro-MBHA resin using NN'-dicyclohexylcarbodiimide (DCC) and N-hydroxybenzotriazole (HOBt). The coupling reaction is carried out for a period of 1 to 18 hr and in an appropriate solvent such as toluene, dichloromethane (DCM), dimethylformamide (DMF) or tetrahydrofuran (THF), or mixtures thereof. The desired peptide chain is assembled by repeating the deprotection, neutralization and coupling reactions using appropriate amino acid derivatives, successively. It is generally known to those skilled in the art that amino acids contain more than one reactive functional group and it is necessary to mask one or more of these groups which are not intended to participate in various steps of SPPS.

Commercially available derivatized amino acids (Peninsula Laboratories; Belmont. California) used for the SPPS of various peptides described in this invention are: Boc-Ala-OH, Boc-D-Ala-OH. Boc-Arg(Tos)-OH. Boc-Asn-OH. Boc-Asp(o-cyclohexyl)-OH. Boc-Asp(OBzl)-OH, Boc-Cys(S-4-MeBzl) -Gln-OH, Boc-Glu(0-cyclohexyl)-OH, Boc-Glu(OBzl)-OH. Boc-Gly -OH, Boc-His(Tos)-OH, Boc-Ile-OH, Boc-Leu-OH, Boc-D-Leu-OH, Boc-Lys(Cl-Z)-OH, Boc-Lys-(Boc)-OH. Boc-Met-OH, Boc-Phe-OH, - Boc-Pro-OH, Boc-Ser(Bzl)-OH. Boc-Thr(Bzl)-OH, Boc-Thr(Bzl) -OH, Boc-Trp-OH, Boc-Tyr(Br-Z)-OH, and Boc-Val-OH. The following derivatives. Boc-1-amino-1-cyclopropane carboxylic acid. Boc-1-amino-1-cyclopentane carboxylic acid, Boc -1-amino-1-cyclohexane carboxylic acid. Boc-1-amino -1-cycloheptane carboxylic acid, and Boc-HN-(CH2)$_n$-COOH, which are not commercially available are prepared by reacting the acylating agent t-butyloxycarbonyl anhydride ([Boc]$_2$-O) with the corresponding amino acid.

After the synthesis. the peptide resin is treated with hydrogen fluoride to release the peptide which is further purified by chromatography. The acid addition salts of the basic amino acid residues are prepared by treatment of the peptide with the appropriate organic or inorganic acid according to procedures well-known to those skilled in the art.

The calcitonin peptides of the invention offer many advantages over natural calcitonins. whether native or synthesized. for use in the treatment of disease.

Many of the synthetic calcitonin peptides disclosed have fewer total amino acids. that is. less than 32. The lower number of residues that have to be incorporated into a synthesized peptide make it more convenient, efficient, and less expensive to manufacture than a synthesized native calcitonin. Further, the lower molecular weight of these calcitonin peptides results in a higher biological activity per mole of administered peptide.

The calcitonin peptides of the invention provide advantages in terms of stability also. A peptide having a disulfide bridge is more difficult to synthesize. The absence of a disulfide bridge in most of these peptides not only eliminates the synthesis problem, but also eliminates a source of instability to storage and a factor in biological inactivation.

Calcitonins lower the blood calcium of immature rats by inhibiting bone resorption. Their potency can be assessed by determining the micrograms of peptide required to reduce the serum calcium by ten percent. The results of in vivo tests of the biological activities of synthetic calcitonin peptides of the invention are shown in Example 37. All of the peptides tested were superior to native human calcitonin in their potency, duration of action, or both.

Therapy

The calcitonin peptides of the invention are used to lower the serum plasma calcium level in patients suffering from diseases associated with elevated serum levels of calcium such as, for example, the hypercalcemia of malignancy and for treating Paget's disease and osteoporosis. These hypocalcemic peptides are administered in amounts ranging from 0.05 to 100 International Units (IU) per kg body weight per day. The peptide may be given as few as one or two days a week or as often as twice daily. A preferred dosage for optimum results would be 0.2 to 10 IU/kg/day. The dosage regimen may be varied according to the clinical indication. For treating the hypercalcemia of malignancy, somewhat higher dosages may be required (5 to 20 IU/kg/day) than with Paget's disease and osteoporosis (0.2 to 2 IU/kg/day). Oral and nasal administration will require dosages 5 to 200 times higher.

Analogues of Other Bioactive Cyclic Peptides

The efficacy of other bioactive cyclic peptides, having structure-activity relationships analogous to that of the calcitonins. may be enhanced by the synthesis of analogues having the potency-enhancing modifications described above for the calcitonins.

According to another aspect of the invention, therefore, we have synthesized analogues of amylin, calcitonin gene related peptide (CGRP), somatostatin, atrial natriuretic peptide, oxytocin and vasopressin wherein the disulfide bridge which forms a cyclic structure has been replaced by a more stable cyclic structure according to the methods of the invention. The analogues of amylin, calcitonin gene related peptide (CGRP), somatostatin, and atrial natriuretic peptide comprise a cyclic structure wherein the cysteine residues that form the disulfide bridge are replaced by a dicarboxylic acid residue and a diamino acid residue linked through side chain groups. according to the synthetic procedure of Example 24. The analogues of oxytocin and vasopressin comprise a cyclic structure wherein one of the cysteine residues of the disulfide bridge at an internal position is replaced by a diamino acid residue and a disulfide bridge forming cysteine at position 1 is replaced by a dicarboxylic acid linked to the side chain of the diamino acid, according to the synthetic procedure of Example 8.

Luteinizing hormone (LHRH) a linear peptide hormone with 10 amino acids. is secreted by the hypothalamus and stimulates the release of LH and FSH by the pituitary gland (Matsuo. H. et al. *Biochem. Biophys. Res. Commun.* 43:1334-1339 (1971)). Structure-activity studies have shown that conformationally restricted analogues of LHRH in which amino acids at positions 1 and 7 are replaced by cysteine residues and linked by a disulfide bridge show superior biological activity (Roeske R. W. et. al. *Peptides: Structure and Function. Proceedings of the 8th American Peptide Symposium* (Hruby, D.J. and Rich, D.H., eds) pp. 333-336 (1983)). Therefore we have synthesized LHRH agonist and antagonist analogues wherein the residues at positions 1 and 7 are replaced by a stable cyclic structure according to the methods of the present invention as described in Example 8.

Atrial natriuretic factors (ANF) are a family of cyclic peptide hormones isolated from the atrial tissue and they exhibit potent diuretic, natriuretic, and vasorelaxant actions (See review: Nutt, R. F. and Weber, D. F., *Clin. Endocrinol. Metab.* 16:19 (1987)). A cysteine disulfide bridge is present between positions 7 and 23 of the atrial peptides and this labile bond is made stable by introducing the alternative cyclic structure described according to the invention.

CGRP is a 37 amino acid single chain polypeptide having a disulfide bridge between positions 1 and 7 and an N-terminal phenylalanine amide residue. There is direct evidence that the peptide acts on the cardiovascular system and has a neurotropic effect on striated muscle. CGRP analogue can be used at dose rates of 0.08 to 200 nmol/kg/hr for hypertension.

Amylin peptide analogues can be used in the treatment of Type I diabetes administered in a dose of 0.2 to 2,000 μg/kg subcutaneously.

Vasopressin peptide analogues can be administered in doses of 0.01 to 40 μg/kg subcutaneously or 0.05 to 200 μg/kg intranasally in the treatment of diabetes insipidus, hemophilia, or von Willebrand's disease.

Somatostatin peptide analogues can be administered in daily doses of 2 to 20.000 μg/kg subcutaneously for the treatment of acromegaly or the watery diarrhea syndrome.

LHRH (agonists) peptide analogues can be used in doses of 2 μg to 120 mg/70 kg daily for female contraception, or the treatment of uterine fibroids, polycystic ovaries, precocious puberty, or endometriosis. Doses 5 to 10 times larger may be used for the same conditions. LHRH (antagonists) are used in an analogous manner for purposes of female contraception.

Oxytocin peptide analogues may be administered at doses of 0.2 to 2000 μg intramuscularly at the time of placental delivery to control bleeding; 0.02 to 400 ng/min. by i.v. continuous infusion to control postpartum uterine bleeding; and 0.24 to 2400 μg intranasally to induce milk production (lactation).

Atrial natriuretic peptide analogues may be administered at doses of 0.01 to 1000 μg/kg/day subcutaneously to reduce aortic blood pressure or to control sodium and water homeostasis. The same peptides at doses of 0.01 to 10 μg/kg/min may also be administered by intravenous infusion.

The peptides of the invention may be administered as free peptides or in the form of pharmaceutically acceptable salts. The active peptides may be administered parenterally, that is by subcutaneous, intramuscular, or intravenous injection. The pharmaceutical formulations suitable for injectable use include sterile aqueous solutions or dispersions and sterile powders for the extemporaneous preparation of sterile injectable solutions or dispersions. In all cases, the form must be sterile and the solution must be fluid to the extent that easy syringability exists. It must be stable under the conditions of manufacture and storage and must be preserved against contaminations of microorganisms, such as for example, bacteria and fungi. The carrier can be a solvent or a dispersion medium containing, for example, water, or a polyol such as glycerol, and suitable mixtures thereof. Compositions for intramuscular use may also contain minor amounts of salts, acids, and bases to adjust tonicity and buffer the solution. Suitable buffering and isotonicity agents are readily determinable by persons skilled in the art.

Oral or nasal administration is also possible especially with analogues which have lipophilic groups or lack the disulfide bridge. Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract. Such oral compositions and preparations should contain at least 0.1% of active peptide, although the percentages of the compositions may vary widely. The amount of therapeutically active compound in such compositions is such that a suitable dosage will be obtained in a convenient volume for ingestion.

Aqueous suspensions may contain the active ingredient in admixture with pharmacologically acceptable excipients, comprising suspending agents, such as methyl cellulose; and wetting agents, such as lecithin or long-chain fatty alcohols. The said aqueous suspensions may also contain preservatives, coloring agents, flavoring agents and sweetening agents in accordance with industry standards.

Liposomal preparations of calcitonin peptides are also useful in enhancing the oral administration as disclosed in U.S. Pat. No. 4,692,433, entitled "Method and Composition for Regulating the Serum Calcium Levels of Mammals," which is hereby incorporated by reference.

Formulations for nasal administration may be in the form of powders or liquids and optionally may contain absorption promoting substances well known to those trained in the art.

The present invention is described below in detail using the following examples, but the methods described are broadly applicable for the preparation of all the peptides described herein and are not limited to the examples given below.

EXAMPLE 1

Synthesis of [(Ser—Thr)₂—Lys-7]-Avian Calcitonin (7-32):

```
              7      8     9    10    11    12    13    14    15    16    17
(Ser—Thr)₂—Lys—Val—Leu—Gly—Lys—Leu—Ser—Gln—Glu—Leu—His—

18    19   20   21   22   23   24   25   26   27   28   29   30   31
Gln—Thr—Tyr—Pro—Arg—Thr—Asp—Val—Gly—Ala—Gly—Ala—Gly—Thr

32
Pro—NH₂
```

Resin Peptide Synthesis

Boc-Pro-MBHA Resin (2 g, 1 mmol) was palced in a reaction vessel of a Beckman 990 B Peptide Synthesizer (Beckman Instruments, Palo Alto, CA.) and subjected to the following operations. Each step was carried out one time unless specified otherwise, and reagents and solvents after each step were separated from the peptide resin by filtration under nitrogen.

| Step | Reagent | Solvent volume | No. of Times | Mix time (minutes) |
|---|---|---|---|---|
| 1. | DCM | 30 ml | 3 times | 1.5 |
| 2. | TFA-DCM (1:1) | 30 ml | | 1.5 |
| 3. | TFA-DCM (1:1) | 30 ml | | 30.0 |
| 4. | DCM | 30 ml | 3 times | 1.5 |
| 5. | Methanol | 30 ml | 3 times | 1.5 |

-continued

| Step | Reagent | Solvent volume | No. of Times | Mix time (minutes) |
|---|---|---|---|---|
| 6. | DCM | 30 ml | 3 times | 1.5 |
| 7. | TFA-DCM (1:1) | 30 ml | | 1.5 |
| 8. | TFA-DCM (1:1) | 30 ml | | 5.0 |
| 9. | DCM | 30 ml | 3 times | 1.5 |
| 10. | DMF | 30 ml | 3 times | 1.5 |
| 11. | Boc-Thr(Bzl)-OH/HOBt/DCC (4 mmol each) in DMF | 20 ml | | 240.0 |
| 12. | DCM | 30 ml | 3 times | 1.5 |
| 13. | Methanol | 30 ml | 3 times | 1.5 |
| 14. | DCM | 30 ml | 3 times | 1.5 |

The coupling reaction was carried out for an average of 4 hours, as in this case, or until a ninhydrin test (Kaiser E.T. et al., *Anal. Biochem.* 34:595-598, 1969) showed a negative result indicatign the absence of free amino grops. The same sequence of reactions was repeated using appropriate amino acid derivatives. Lysine at position 7 was incorporated using Boc-Lys(Boc)-OH. and the subsequent two derivatives. Boc-Thr(Bzl)-OH and Boc-Ser(BZl)-OH were coupled using 10 mmol of each derivative, HOBt and DCC. After completion of the synthesis, the resin was removed from the vessel and dried under vacuum.

Cleavage of the Resin-Peptide using Hydrogen Fluoride (HF)

The dried peptide resin (1 g), anisole (1 ml) and p-cresol (0.1 g) were placed in a Kel-F reaction vessel. The vessel was placed in a bath of liquid nitrogen and anhydrous HF (15 ml) was condensed into the vessel. The reaction mixture was stirred at $-10°$ C. for 1 hour and HF was removed by evaporation under vacuum. The residue was triturated with dry ether (50 ml), filtered and washed with additional quantities of ether (3×50 ml). Peptide product in the mixture was isolated by extracting with glacial acetic acid (3×50 ml) followed by lyophilization to remove the solvent.

Peptide Purification

Peptide powder from the HF cleavage (200 mg) was dissolved in 1N acetic acid (3 ml), loaded onto a Sephadex G-25 (superfine) column (1.5 cm×100 cm) and eluted with 1N acetic acid. The eluent fractions containing the peptide were pooled and freeze dried. The resulting peptide (50 mg) was further purified by preparative reverse phase high performance chromatography (RP-HPLC) using a Waters C-4 column and a buffer gradient of 0.1% TFA in water to 70% acetonitrile in 0.1% TFA in water. The fractions containing pure peptide (determined by analytical HPLC) were combined and the product isolated by lyophilization. Purity of peptide was better than 95% by HPLC; and amino acid analysis followed by acid hydrolysis (6N HCl, 110° C., 24 hr) gave expected amino acid ratios.

EXAMPLE 2

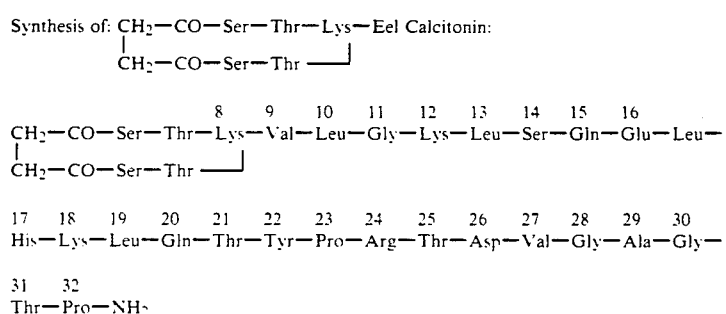

Starting from Boc-Pro-MBHA resin (2 g, 1mmol) the peptide chain was assembled until the valine at position 8 was incorporated as described in Example 1. At this point, the lysine residue was introduced using Boc-Lys(Fmoc)-OH, and the synthesis was continued using Boc-Thr(Bzl)-OH and Boc-Ser(Bzl)-OH. The product following deprotection and neutralization (steps 1 through 10) was subjected to the following steps:

1. succinic anhydride (20 mmol) in DCM (30 ml) for 4h;
2. DCM wash (3×50 ml);
3. DMF wash (3×50 ml);
4. 50% piperidine-DMF (2×50 ml) for 2 hours,;
5. DCC-DCM (30 mmol) for 8 hours;
6. DCM wash (3×50 ml);
7. DMF wash (3×50 ml); and
8. DCM wash (3×50 ml).

The resin was then filtered and dried under vacuum. Cleavage of the peptide from the resin, purification and characterization was carried out as described in Example 1.

EXAMPLE 3

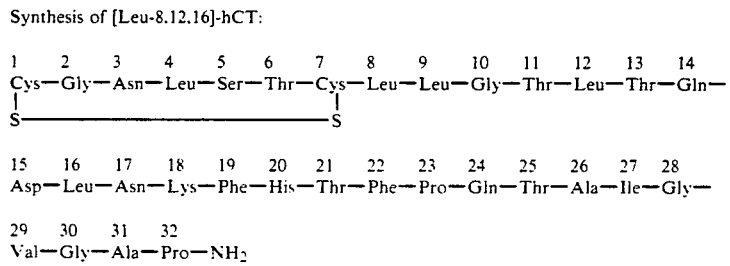

Starting from Boc-Pro-MBHA resin (2g. 1mmol). the peptide chain was assembled and cleaved from the resin using HF as described in Example 1. The linear peptide, containing free sulfhydryl groups in the cysteine residues at positions 1 and 7, was dissolved in distilled water 1 mg per 5 ml) and subjected to air oxidation at pH 7.5 for 24 hours. The cyclized product obtained was purified and characterized as above.

EXAMPLE 4

Synthesis of [(Leu—Ala—Ser—Asn—Leu—Ser—Thr)$_2$—Lys$^7$, Leu$^8$]—Eel Calcitonin (7-32):

```
                                7   8   9   10  11  12  13
(Leu—Ala—Ser—Asn—Leu—Ser—Thr)₂—Lys—Leu—Leu—Gly—Lys—Leu—Ser—

14  15  16  17  18  19  20  21  22  23  24  25  26  27  28
Gln—Glu—Leu—His—Lys—Leu—Gln—Thr—Tyr—Pro—Arg—Thr—Asp—Val—Gly 29  30  31  32
Ala—Gly—Thr—Pro—NH₂
```

Starting from Boc-Pro-MBHA resin (2 g, 1 mmol), the peptide chain was assembled until the amino acid leucine at position 9 as described in Example 1. Synthesis was then continued using consecutively, the following protected amino acid derivatives: Boc-Leu-OH.H$_2$O, Boc-Lys(Boc)-OH. Boc-Thr(BZl)-OH. Boc-Ser(Bzl)-OH. Boc-Leu-OH.H$_2$O. The peptide resin was subjected to HF reaction, and the isolated peptide was purified and characterized according to the procedure described in Example 1.

EXAMPLE 5

Synthesis of [(Chx—Ser—Thr)$_2$—Lys$^7$, Leu$^8$]-Eel Calcitonin (7-32):

```
                  7  8  9
(Chx—Ser—Thr)₂—Lys—Leu—Leu—Gly—Lys—Leu—Ser—Gln—Glu—Leu—His—

Lys—Leu—Gln—Thr—Tyr—Pro—Arg—Thr—Asp—Val—Gly—Ala—Gly—Thr—Pro—NH₂
```

Starting from Boc-Pro-MBHA resin (2 g, 1 mmol), the peptide chain was assembled until the amino acid leucine at position 9 as described in Example 1. Synthesis was then continued using consecutively, the following protected amino acid derivatives: Boc-Leu-OH.H$_2$O, Boc-Lys(Boc)-OH, Boc-Thr(Bzl) -OH, Boc-Ser(Bzl)-OH. The Boc-group from the resin was removed using trifluoroacetic acid and the product coupled with cyclohexyl propionic acid using DCC as condensing agent. The resin obtained was subjected to HF reaction, and the isolated peptide was purified and characterized according to the procedure described in Example 1.

The structure [(Chx-Ser-Thr)$_2$-Lys$^7$, Leu$^8$]-Eel Calcitonin (7-32) represented in Example 5 also represents the analog: [(Chx-Ser-Thr)$_2$-Lys$^7$, Leu$^8$]-Avian Calcitonin (7-32).

EXAMPLE 6

Synthesis of (Leu$^8$)-Eel Calcitonin:

```
                                    8
Cys—Ser—Asn—Leu—Ser—Thr—Cys—Leu—Leu—Gly—Lys—Leu—Ser—Gln—
 |                       |
 S———————————————————————S

Glu—Leu—His—Lys—Leu—Gln—Thr—Tyr—Pro—Arg—Thr—Asp—Val—Gly—

Ala—Gly—Thr—Pro—NH₂
```

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 3.

EXAMPLE 7

Synthesis of ((Leu—Cys)$^1$, Leu$^8$)-Eel Calcitonin:

```
 1                                   8
Leu—Cys—Ser—Asn—Leu—Ser—Thr—Cys—Leu—Leu—Gly—Lys—Leu—Ser—
     |                       |
     S———————————————————————S

Gln—Glu—Leu—His—Lys—Leu—Gln—Thr—Tyr—Pro—Arg—Thr—Asp—Val—

Gly—Ala—Gly—Thr—Pro—NH₂
```

The title peptide was prepared according to Example 6.

EXAMPLE 8

Synthesis of CH₂—CO—Ser—Asn—Leu—Ser—Thr—NH—CH—CO—Leu)⁸-Eel Calcitonin (8-32):
 |
 CH₂—CO—NH—CH₂—CH₂—CH₂—CH₂——┘

CH₂—CO—Ser—Asn—Leu—Ser—Thr—NH—CH—CO—Leu—Leu—Gly—Lys—Leu—┐
 |                                                                                                                                                    │
 CH₂—CO—NH—CH₂—CH₂—CH₂—CH₂——┘                                                                                            │
                                                                                                                                                      │
     ┌─────────────────────────────────────────────────────────────────────────────┘
     └—Ser—Gln—Glu—Leu—His—Lys—Leu—Gln—Thr—Tyr—Pro—Arg—Thr—Asp—┐
                                                                                                                                          │
     ┌─────────────────────────────────────────────────────────────────────┘
     └—Val—Gly—Ala—Gly—Thr—Pro—NH₂

Starting from Boc-Pro-MBHA resin (2 g, 1 mmol), the peptide chain was assembled until the leucine at position 9 was incorporated as described in Example 1. Synthesis was then continued using consecutively, the following protected amino acid derivatives: Boc-Leu-OH.H₂O, Boc-Lys(Fmoc)-OH, Thr(Bzl)-OH, Boc-Ser Boc-Bzl)-OH, Boc-Leu-OH.H₂O, Boc-Asn-OH, and Boc-Ser(Bzl)-OH. The resulting peptide resin was subjected to the following operations:

1. DCM Wash (3×50 ml)
2. DMF Wash (3×50 ml)
3. Piperidine-DMF (1:1) (1×50 ml, 1.5 min)
4. Piperidine-DMF (1:1) (1×50 ml, 20 min)
5. DMF Wash (3×50 ml)
6. DCM Wash (3×50 ml)
7. Succinic Anhydride (20 mmol) in DCM for 4 hour
8. DMF Wash (3×50 ml)
9. DCM Wash (3×50 ml)
10. TFA-DCM (1:1) (1×50 ml, 1.5 min)
11. TFA (1:1) (1×50 ml, 30 min)
12. DCM Wash (3×50 ml)
13. Methanol Wash (3×50 ml)
14. DCM Wash (3×50 ml)
15. TEA (1:9) (1×50 ml, 1.5 min)
16. TEA (1:9) (1×50 ml, 5 min)
17. DCM Wash (3×50 ml)
18. DCC-DCM (30 mmol) for 20 hours
19. DMF Wash (3×50 ml)
20. DCM Wash (3×50 ml)
21. Methanol Wash (3×50 ml)

The resin was then filtered and dried under vacuum. Cleavage of the peptide from the resin, purification and characterization of the product was carried out as described in Example 1.

EXAMPLE 9

Synthesis of [(Acetyl-Aoa—Ser—Thr)₂—Lys⁷, Leu⁸]-Avian Calcitonin (7-32):

7  8  9
(Acetyl-Aoa—Ser—Thr)₂—Lys—Leu—Leu—Gly—Lys—Leu—Ser—Gln—Glu—

Leu—His—Lys—Leu—Gln—Thr—Tyr—Pro—Arg—Thr—Asp—Val—Gly—Ala—

Gly—Thr—Pro—NH₂

This peptide was synthesized by following the procedure described in Example 5 except using Boc-8-amino octanoic acid in the place of cyclohexylpropionic acid, removing the Boc-group using trifluoroacetic acid and acetylating the product using acetic anhydride.

The structure [(Acetyl-Aoa-Ser-Thr)₂-Lys⁷, Leu⁸-Avian Calcitonin (7-32) also represents the eel calcitonin analogue: (Acetyl-Aoa-Ser-Thr)₂-Lys₂-Lys⁷, Leu⁸]-Eel Calcitonin (7-32)

EXAMPLE 10

Synthesis of [(D-Ala—Ada—Ser)⁵, Ala⁷, des-²²]-Avian Calcitonin (5-32):

7  8  9
(D-Ala—ADA—Ser)₅—Thr—Ala—Val—Leu—Gly—Lys—Leu—Ser—Gln—Glu—Leu—

His—Lys—Leu—Gln—Thr—Pro—Arg—Thr—Asp—Val—Gly—Ala—Gly—Thr—Pro—NH₂

This compound was prepared starting from Boc-Pro-MBHA resin (2 g, 1 mmol) and using appropriate amino acid derivatives following the procedure described in Example 1 except the coupling step with Boc-Tyr(Br-Z)-OH at position 22 was eliminated.

The structure [(D-Ala-Ada-Ser)⁵, Ala⁷, des-²²]-Avian Calcitonin (5-32) also represents the eel analogue: [(D-Ala-Ada-Ser)⁵, Ala⁷, des-²²]-Eel Calcitonin (5-32).

EXAMPLE 11

Synthesis of [(Chx—Ser)⁵, Ala⁷, des-²²]Avian Calcitonin (5-32):

7  8  9
[Chx—Ser]⁵—Thr—Ala—Val—Leu—Gly—Lys—Leu—Ser—Gln—Glu—Leu—His—

Lys—Leu—Gln—Thr—Pro—Arg—Thr—Asp—Val—Gly—Ala—Gly—Thr—Pro—NH₂

This peptide was prepared according the procedure described in Example 5.

The structure [(Chx-Ser)⁵, Ala⁷, des-²²]-Avian Calcitonin (5-32) also represents the eel calcitonin analogue: [Chx-Ser)⁵, Ala⁷, des-²²]-Eel Calcitonin (5-32).

EXAMPLE 12

Synthesis of [Leu⁸,¹²]-Human Calcitonin:

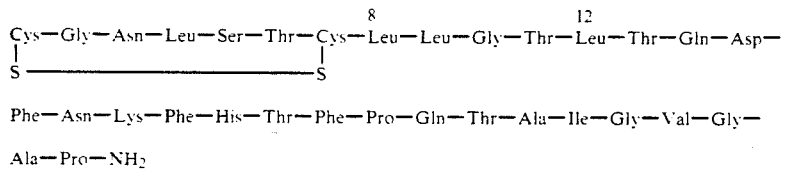

This peptide was prepared accoding to the proceudre described for [Leu⁸,¹²,¹⁶]-hCT in Example 3.

EXAMPLE 13

Synthesis of [(Leu—Cys)¹, Leu⁸,¹²]-Human Calcitonin:

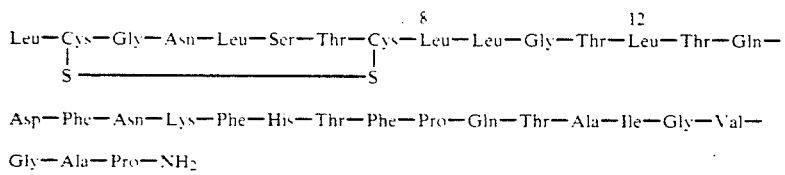

This peptide was prepared according to the procedure described for the preparation of [Leu⁸,¹²,¹⁶]-hCT in Example 3.

EXAMPLE 14

Synthesis of [Leu—Cys)¹, Leu⁸,¹²,¹⁶]-Human Calcitonin:

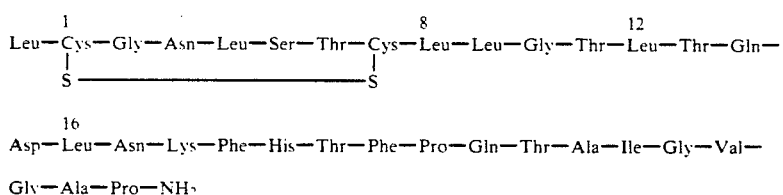

This peptide was prepared according to the procedure described for the preparation of [Leu⁸,¹²,¹⁶]-hCT in Example 3.

EXAMPLE 15

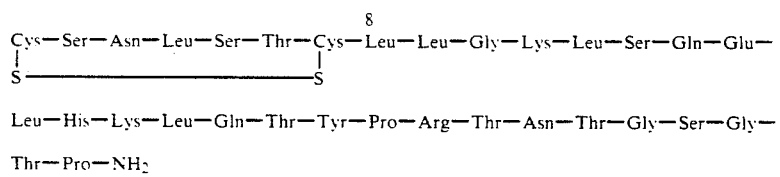

Starting from Boc-Pro-MBHA resin (2 g, 1 mmol), the peptide chain was assembled using appropriate protected amino acid derivatives. Cleavage of the peptide from the resin, formation of the disulfide bridge, and its purification and characterization was carried out according the procedure described in Example 3.

EXAMPLE 16

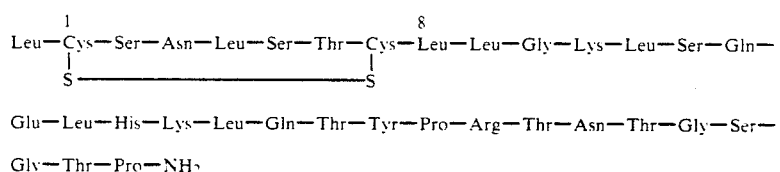

The title peptide was prepared according to Example 6 above.

EXAMPLE 17

Synthesis of [Leu—Ala—Ser—Asn—Leu—Ser—Thr)₂—Lys⁷, Leu⁸]-Salmon Calcitonin (7-32):

(Leu—Ala—Ser—Asn—Leu—Ser—Thr)₂—Lys—Leu—Leu—Gly—Lys—Leu—Ser—

Gln—Glu—Leu—His—Lys—Leu—Gln—Thr—Tyr—Pro—Arg—Thr—Asn—Thr—Gly—

Ser—Gly—Thr—Pro—NH₂

The title peptide was prepared according to the procedure described in Example 4 above.

EXAMPLE 18

Synthesis of [(Chx—Ser—Thr)₂—Lys⁷, Leu⁸]-Salmon Calcitonin (7-32):

(Chx—Ser—Thr)₂—Lys—Leu—Leu—Gly—Lys—Leu—Ser—Gln—Glu—Leu—His—

Lys—Leu—Gln—Thr—Tyr—Pro—Arg—Thr—Asn—Thr—Gly—Ser—Gly—Thr—

Pro—NH₂

The title peptide was prepared according to the procedure described in Example 4 above.

EXAMPLE 19

Synthesis of (CH₂—CO—Ser—Asn—Leu—Ser—Thr—NH—CH—CO—Leu)⁸-Salmon CT(8-32):
|                                                                            |
CH₂—CO—NH—CH₂—CH₂—CH₂—CH₂—┘

(CH₂—CO—Ser—Asn—Leu—Ser—Thr—NH—CH—CO—Leu—Leu—Gly—Lys—Leu—
|                                                                            
CH₂—CO—NH—CH₂—CH₂—CH₂—CH₂—┘

Ser—Gln—Glu—Leu—His—Lys—Leu—Gln—Thr—Tyr—Pro—Arg—Thr—Asn—

Thr—Gly—Ser—Gly—Thr—Pro—NH₂

This peptide was prepared according to the procedure described in Example 8.

EXAMPLE 20

Synthesis of [(Leu—Ala—Ala—Ser—Leu—Ser—Thr)₂—Lys⁷.Leu⁸]—

Avian Calcitonin (7-32):

(Leu—Ala—Ala—Ser—Leu—Ser—Thr)₂—Lys—Leu—Leu—Gly—Lys—Leu—Ser—

Gln—Glu—Leu—His—Lys—Leu—Gln—Thr—Tyr—Pro—Arg—Thr—Asp—Val—

Gly—Ala—Gly—Thr—Pro—NH₂

This compound was prepared according to the procedure described in Example 4.

EXAMPLE 21

Synthesis of (Leu⁸)-Avian Calcitonin:

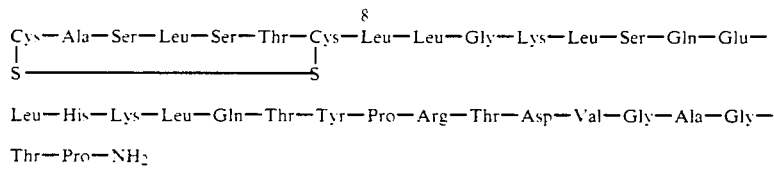

Leu—His—Lys—Leu—Gln—Thr—Tyr—Pro—Arg—Thr—Asp—Val—Gly—Ala—Gly—

Thr—Pro—NH₂

The preparation of this peptide was carried out according to the method described in Example 6.

EXAMPLE 22

Synthesis of ((Leu—Cys)¹, Leu⁸)-Avian Calcitonin:

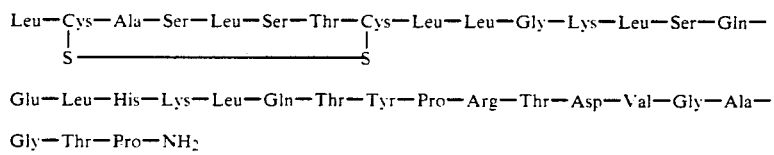

Glu—Leu—His—Lys—Leu—Gln—Thr—Tyr—Pro—Arg—Thr—Asp—Val—Gly—Ala—

Gly—Thr—Pro—NH₂

This peptide was prepared according the procedure described in Example 7.

EXAMPLE 23

Synthesis of (CH$_2$—CO—Ala—Ser—Leu—Ser—Thr—NH—CH—CO—Leu)$^8$-Avian CT (8-32):
|
CH$_2$—CO—NH—CH$_2$—CH$_2$—CH$_2$—CH$_2$—┘

(CH$_2$—CO—Ala—Ser—Leu—Ser—Thr—NH—CH—CO—Leu—Leu—Gly—Lys—Leu—Ser—
|
CH$_2$—CO—NH—CH$_2$—CH$_2$—CH$_2$—CH$_2$—┘

Gln—Glu—Leu—His—Lys—Leu—Gln—Thr—Tyr—Pro—Arg—Thr—Asp—Val—Gly—

Ala—Gly—Thr—Pro—NH$_2$

This peptide was prepared according to the method described in Example 8.

EXAMPLE 24

Synthesis of (Lys—NH—CH—CO—Asn—Thr—Ala—Thr—NH—CH—CO—Ala)$^8$ Rat Amylin(8-37):
|
CH$_2$—CH$_2$—CO—NH—(CH$_2$)$_4$—┘

(Lys—NH—CH—CO—Asn—Thr—Ala—Thr—NH—CH—CO—Ala—Thr—Gln—Arg—Leu—Ala—
|
CH$_2$—CH$_2$—CO—NH—(CH$_2$)$_4$—┘

Asn—Phe—Leu—Val—Arg—Ser—Ser—Asn—Asn—Leu—Gly—Pro—Val—Leu—Pro—

Pro—Thr—Asn—Val—Gly—Ser—Asn—Thr—Tyr—OH

Starting from Boc-Tyr(Br-Z)-O-Resin (2 g, 1 mmol; Omni Biochem, San Diego, CA), the peptide chain was assembled until the alanine residue at position 8 as described in Example 1. Synthesis was continued by incorporating the amino acid derivatives, Boc-Lys(Fmoc)-OH, Boc-Thr(Bzl)-OH, Boc-Ala-OH, Boc-Thr(Bzl)-OH and Boc-Asn-OH, consecutively to obtain the resin: Boc-Asn-Thr(Bzl)-Ala-Thr(Bzl)-Lys(Fmoc) -(9-37)-Rat Amylin-Polymer.

The Fmoc-group present on the epsilon amino group of lysine at position 7 was deprotected using piperidine - DMF (1:1) as described Example 8. Next, Fmoc-Aspartic acid-alpha-t-butyl ester was coupled using DCCD as condensing agent. The product,

```
      ┌─────────────────────────────────────────────────────────┐
Fmoc—Asp—O—tBu        Boc—Asn—Thr(Bzl)—Ala—Thr(Bzl)—Lys—(9-37)-Rat Amylin-Polymer.
``` was treated with trifluoroacetic acid to deprotect the alpha amino group of asparagine at position 3 as well as the alpha carboxyl group of aspartic acid at position 2. These groups were then linked using DCC. The Fmoc protecting moiety from the product was cleaved using piperidine-DMF (1:1) and the last amino acid was introduced as Boc-Lys(Boc)-OH. Cleavage of the peptide from the resin and purification was carried out as described in Example 1.

EXAMPLE 25

Synthesis of (Lys—NH—CH—CO—Asn—Thr—Ala—Thr—NH—CH—CO—Ala)$^8$ Human Amylin
|                                                              (8-37)
CH$_2$—CH$_2$—CO—NH—(CH$_2$)$_4$—┘

Lys—NH—CH—CO—Asn—Thr—Ala—Thr—NH—CH—CO—Ala—Thr—Gln—Arg—Leu—
|
CH$_2$—CH$_2$—CO—NH—(CH$_2$)$_4$—┘

Ala—Asn—Phe—Leu—Val—His—Ser—Ser—Asn—Asn—Phe—Gly—Ala—Ile—Leu—
Ser—Ser—Thr—Asn—Val—Gly—Ser—Asn—Thr—Tyr—OH

Starting from Boc-Tyr-(Br-Z)-O-Resin (2 g, 1 mmol) the title peptide was synthesized as described in Example 24.

EXAMPLE 26

Synthesis of (Lys—NH—CH—CO—Asn—Thr—Ala—Thr—NH—CH—CO—Ala)$^8$ - Rat Amylin
|                                                              (8-37) Amide
CH$_2$—CH$_2$—CO—NH—(CH$_2$)$_4$—┘

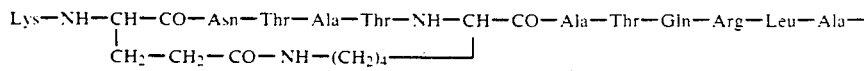

Asn—Phe—Leu—Val—Arg—Ser—Ser—Asn—Asn—Leu—Gly—Pro—Val—Leu—Pro—
Pro—Thr—Asn—Val—Gly—Ser—Asn—Thr—Tyr—NH$_2$

Starting from Boc-Tyr-(Br-Z)-MBHA-Resin (2 g, 1 mmol) the title peptide was synthesized as described in Example 24.

EXAMPLE 27

Synthesis of

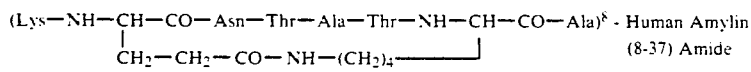 - Human Amylin (8-37) Amide

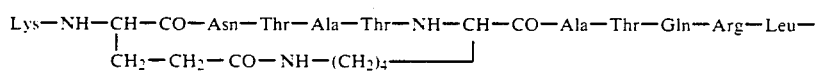

Ala—Asn—Phe—Leu—Val—His—Ser—Ser—Asn—Asn—Phe—Gly—Ala—Ile—
Leu—Ser—Ser—Thr—Asn—Val—Gly—Ser—Asn—Thr—Tyr—NH$_2$

Starting from Boc-Tyr-(Br-Z)-MBHA-Resin (2 g, 1 mmol) the title peptide was synthesized as described in Example 24.

EXAMPLE 28

Synthesis of
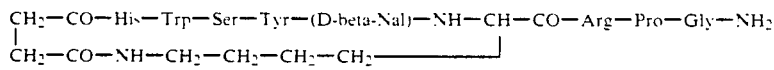

The title compound, a novel cyclic analog of the luteinizing hormone releasing hormone (LHRH) agonist ((D-beta-Naphthylalanine) 6-LHRH; Nafarelin$^R$), was prepared starting from Boc-Gly-MBHA Resin (2 g, 1 mmol; Omni Biochem, San Diego, CA) and following the procedure described in Example 8.

EXAMPLE 29

Synthesis of
CH$_2$—CO—(D—Phe)—Trp—Ser—Tyr—(D-beta-Nal)—NH—CH—CO—Arg—Pro—Gly—NH$_2$
|⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯|
CH$_2$—CO—NH—CH$_2$—CH$_2$—CH$_2$—CH$_2$⎯⎯⎯⎯⎯⎯⎯⎯⎯⎯|

The title compound, a novel cyclic analog of the luteinizing hormone releasing hormone (LHRH) antagonist ((D-Phe)$^2$ (D-beta-Naphthylalanine)$^6$-LHRH), was prepared starting from Boc-Gly-MBHA Resin (2 g, 1 mmol; Omni Biochem, San Diego, CA) and following the procedure described in Example 8.

EXAMPLE 30

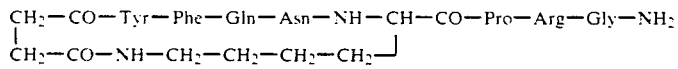

The title compound, a novel cyclic analog of the diuretic hormone vasopressin, was prepared starting from Boc-Gly -MBHA Resin (2 g, 1 mmol) and following the procedure described in Example 8.

EXAMPLE 31

Synthesis of
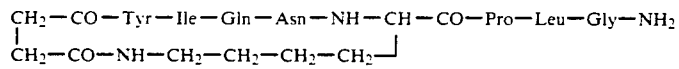

The title compound, a novel cyclic analog of the peptide hormone oxytocin, was prepared starting from Boc-Gly-MBHA Resin (2 g, 1 mmol) and following the procedure described in Example 8.

EXAMPLE 32

Synthesis of

-continued

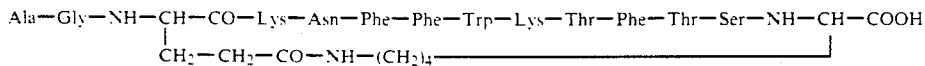

The title compound, a novel cyclic analog of somatostatin, was prepared starting from Boc-Lys(Fmoc)-O-CH₂-Resin (2 g, 1 mmol, Omni Biochem, San Diego, CA) and following the procedure described in Example 24.

EXAMPLE 33

Synthesis of

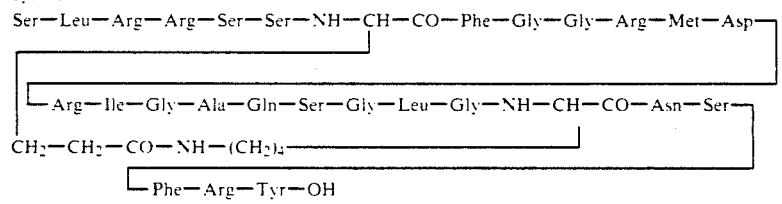

Starting from Boc-Tyr(Br-Z)-O-Resin (2 g, 1 mmol), the title peptide, a novel cyclic analogue of human atrial natriuretic peptide, was synthesized as described in Example 24.

EXAMPLE 34

Synthesis of a Cyclic Rat Atrial Natriuretic Peptide

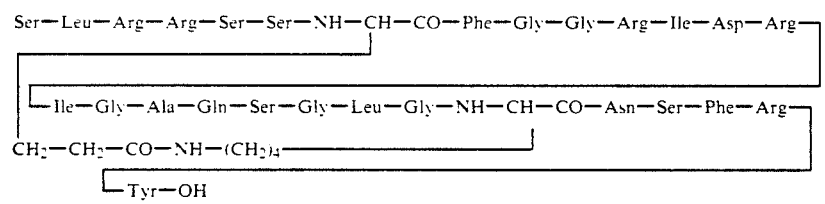

Starting from a Boc-Tyr-(Br-Z)-O-Resin (2 g, 1 mmol), the title peptide, a novel cyclic analog of rat atrial natriuretic peptide was synthesized as described in Example 24.

EXAMPLE 35

Synthesis of

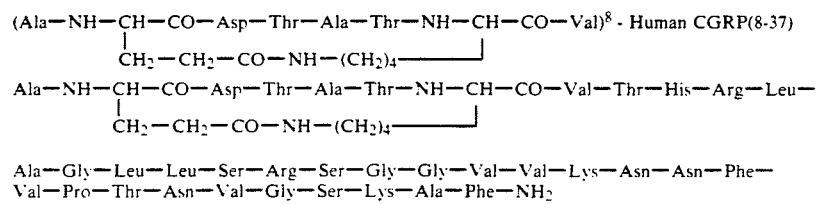

Starting from Boc-Phe-MBHA Resin (2 g, 1 mmol), the title peptide, a novel cyclic analogue of human calcitonin gene related peptide, was synthesized as described in Example 24.

EXAMPLE 36

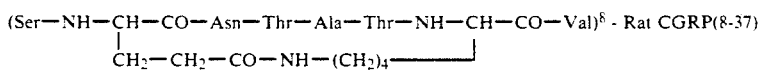
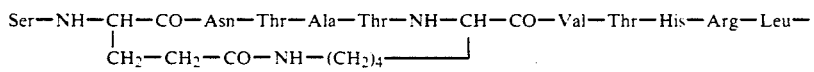
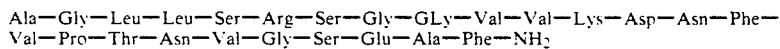

Starting from Boc-Phe-MBHA Resin (2g, 1 mmol), the title peptide, a novel cyclic analog of rat calcitonin gene related peptide, was synthesized as described in Example 24.

EXAMPLE 37

Biological Assay of Synthetic Calcitonin Peptides

Peptides of the Formula I exhibit valuable hypocalcemic activity. This activity was measured as follows: Male rats (Sprague Dawley) weighing approximately 100 grams were fasted overnight. Peptides according to the invention, comprising various potency-enhancing modifications, were dissolved in pH 7.4 PBS buffer at a concentration range of 0.001 microgram to about 100 microgram per ml. The rats were anesthetized with Metophane10, weighed and injected subcutaneously with the peptide solutions in a dose of from 0.001 to about 100 microgram per kilogram of body weight. After varying periods of time the animals were anesthetized and an abdominal incision was made; blood samples were taken from the inferior vena cavae and the serum was analyzed for calcium by the method of Liedtke, Clinical Chemistry, 27, 2025-2028 (1981). Calcium-lowering potencies of the synthetic peptides can be calculated in International units (IU) per mg as described by the method of M. Kumar et al., *J. Endocrinology* 33:469-475 (1964). According to this test, 10 IU is defined as the amount of peptide necessary for lowering $Ca++$ concentration by 10% in 100 gram rats one hour after subcutaneous injection. Serum $Ca++$ levels in the rat after subcutaneous injection of various peptides are summarized below:

| Compound | Dose ug/kg | Time | $Ca^{++}$ Decrease mg/dl |
|---|---|---|---|
| [(Ser—Thr)$_2$-Lys-7]-cCT(7-32) | 1 | 1 hr | 2.09 |
| | 10 | 1 hr | 2.75 |
| | 100 | 1 hr | 2.75 |
| [(AcOAOA-Ser—Thr)$_2$-Lys-7]-cCT(7-32) | 0.1 | 1 hr | 0.42 |
| | 0.4 | 1 hr | 0.45 |
| | 1 | 1 hr | 2.29 |
| | 10 | 1 hr | 2.45 |
| | 100 | 1 hr | 2.34 |
| [(D-Ala-ADA-Ser)-5,Ala-7,des-22]-cCT(5-32) | 1 | 1 hr | 0.32 |
| | 10 | 1 hr | 1.42 |
| | 100 | 1 hr | 1.82 |
| [(CHX-Ser)-5,Ala-7,des-22]-cCT(5-32) | 1 | 1 hr | 0.32 |
| | 10 | 1 hr | 1.42 |
| | 100 | 1 hr | 1.82 |
| [(Oleyl-Ser)-5,Ala-7]-cCT(5-32) | 1 | 1 hr | 0.47 |
| | 10 | 1 hr | 0.60 |
| | 100 | 1 hr | 1.15 |
| [(ADA-Ser)-5,Ala-7]-cCT(5-32) | 1 | 1 hr | 0.19 |
| | 3 | 1 hr | 0.33 |
| | 10 | 1 hr | 2.83 |
| | 1 | 3 hr | 0.14 |
| | 3 | 3 hr | 0.21 |
| | 10 | 3 hr | 2.98 |
| | 10 | 6 hr | 2.10 |
| [Leu-8,12]-hCT | 0.1 | 1 hr | 0.37 |
| | 0.3 | 1 hr | 1.17 |
| | 1 | 1 hr | 2.05 |
| | 3 | 1 hr | 2.13 |
| | 10 | 1 hr | 2.81 |
| | 10 | 3 hr | 1.98 |
| [Leu-8,12,16]-hCT | 0.1 | 1 hr | 0.03 |
| | 0.3 | 1 hr | 0.92 |
| | 1 | 1 hr | 1.92 |
| | 3 | 1 hr | 2.12 |
| | 10 | 1 hr | 3.05 |
| | 10 | 1 hr | 2.00 |
| | 10 | 6 hr | 1.72 |
| [(Leu—Ala—Ser—Asn—Leu—Ser—Thr)$_2$-Lys$^7$, Leu$^8$]-eCT(7-32) | 0.01 | 1 hr | 0.64 |
| | 0.03 | 1 hr | 0.82 |
| | 0.1 | 1 hr | 1.84 |
| | 0.32 | 1 hr | 2.64 |
| | 1.0 | 1 hr | 3.19 |
| [(Chx—Ser—Thr)$_2$-Lys$^7$, Leu$^8$]-eCT(7-32) | 0.01 | 1 hr | 0.13 |
| | 0.03 | 1 hr | 0.24 |
| | 0.1 | 1 hr | 0.39 |
| | 0.32 | 1 hr | 1.09 |
| | 1.0 | 1 hr | 2.42 |
| (Leu$^8$)-eCT | 0.01 | 1 hr | 0.15 |
| | 0.32 | 1 hr | 1.02 |
| | 0.1 | 1 hr | 1.82 |
| | 1.0 | 1 hr | 2.90 |
| [(Leu—Cys)$^1$, Leu$^8$]-eCT | 0.1 | 1 hr | 0.33 |
| | 0.03 | 1 hr | 1.24 |
| | 0.1 | 1 hr | 2.34 |
| | 1.0 | 1 hr | 3.35 |
| (CH$_2$—CO—Ser—Asn—Leu—Ser—Thr—NH—CH—CO—Leu)$^8$-eCT(8-32)<br>\|<br>CH$_2$—CO—NH—CH$_2$—CH$_2$—CH$_2$—CH$_2$⎦ | 0.01 | 1 hr | 0.05 |
| | 0.03 | 1 hr | 0.17 |
| | 0.1 | 1 hr | 1.48 |
| | 0.32 | 1 hr | 2.68 |
| Human CT | 1.0 | 1 hr | 0.02 |
| | 3.2 | 1 hr | 0.54 |
| | 10.0 | 1 hr | 1.59 |
| Avian CT | 0.01 | 1 hr | 0.18 |
| | 0.03 | 1 hr | 0.22 |

-continued

| Compound | Dose ug/kg | Time | Ca⁻⁻Decrease mg/dl |
|---|---|---|---|
|  | 0.1 | 1 hr | 1.39 |
|  | 0.32 | 1 hr | 2.76 |
| Salmon CT | 0.01 | 1 hr | 0.82 |
|  | 0.03 | 1 hr | 1.52 |
|  | 0.1 | 1 hr | 2.40 | cCT: chicken calcitonin
hCT: human calcitonin
eCT: eel calcitonin

EXAMPLE 38

Nasal Bioavailability of Hypocalcemic Peptides

Peptides of the formula I when administered intranasally show hypocalcemic effects in animals. In order to determine their bioavailability, the effect of hypocalcemic peptides administered intranasally were compared with those administered by intravenous injection, as described below. Nasal powdery formulations containing 100 IU per 30 mg of dry powder were prepared substantially as described in U.S. Pat. No. 4,613,500. Peptides were administered intranasally at a dose of 2.8 IU/kg or intravenously at a dose of 1.75 IU/kg to rabbits. Blood samples were withdrawn before administering the peptides and 0.5, 1, 2, 4, and 6 hours after administration, and serum calcium levels determined. The ratios of areas under the curve of hypocalcemic effect (0 to 6 hours) after nasal and intravenous administration are calculated.

| Compound | Ratio of Nasal:i.v. Bioavailability |
|---|---|
| [Leu$^{8,12,16}$]-hCT | 28.0% |
| (CH$_2$—CO—Ser—Asn—Leu—Ser—Thr—NH—CH—CO—Leu)$^8$-eCT<br>\|<br>CH$_2$—CO—NH—CH$_2$—CH$_2$—CH$_2$—CH$_2$—⎦ | 14.3% |
| (Leu$^8$)-eCT | 28.6% |
| [(Leu—Cys)$^1$, Leu$^8$]-eCT | 37.5% |
| [(Chx—Ser—Thr)$_2$-Lys$^7$, Leu$^8$]-eCT | 17.4% |

It should be apparent from the foregoing that various peptide analogues, including calcitionin analogues and those of other bioactive peptide analogues may be substituted in the Examples to obtain similar results.

Accordingly, the invention may be embodied in other specific forms without departing from it in spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A branched hypocalcemic peptide of the formula

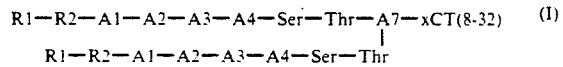

wherein
R1 is H, H—(CH$_2$)$_n$—CO—; H2N—(CH2)$_n$—CO—; Z—CO—(CH2)$_n$—CO—, wherein Z is HO—, cholesterol, adamantyl alcohol, or an aromatic alcohol; L-threonine or D-threonine; L-alanine; D-alanine; L-leucine; D-leucine; cyclopropane carboxyl (CPRC); cyclopentane carboxyl (CPC); cyclohexane carboxyl (CHC); cyclohexylpropionyl (CHX); cycloheptane carboxyl (CHPT); adamantaneacetyl (ADM); adamantane carboxyl (ADC); or acyl groups of armomatic or heterocyclic carboxylic acids;

R2 is 1-amino-1-cyclopropane carboxyl (ACPR); 1-amino-1-cyclopentane carboxyl (ACPC); 1-amino 1-cyclohexane carboxyl (ACHC); 1-amino-1-cycloheptane carboxyl (ACHP); no moiety; or is the same as R1;

A1 is L-cysteine; L-threonine; D-threonine; L-tyrosine; D-tyrosine; L-alanine; D-alanine; L-leucine; D-leucine; or 2-aminoisobutyric acid; or mercaptopropionic acid; mercaptoacetic acid; H—(CH$_2$-)$_n$—CO—; 1-amino-1-cyclopropane carboxyl; 1-amino-1-cyclopentane carboxyl; 1-amino-1-cyclohexane carboxyl; 1-amino-1-cycloheptane carboxyl; or no moiety;

n = 1 to 22;

A2 is glycine; L-alanine; L-serine; or no moiety;

A3 is L-asparagine; L-serine; or no moiety;

A4 is L-leucine; or no moiety; and

A7 is L-lysine; L-orginine; or Ornithine; and wherein xCT is an amino acid sequence corresponding at least at residues 9-11, 13-15, 17, 18, 23-26, and 28-32 to murine, salmon, eel, avian, procine, bovine, ovine, or human calcitonin, or pharmaceutically acceptable salts thereof.

2. The hypocalcemic branched peptide of claim 1, wherein A7 is lysine or ornithine, comprising two peptide sequences of the formula R1-R2-A1-A3-A4-Ser-thr attched to A7 by peptide linkages between the Thr carboxyl groups and the amino groups of A7, one said peptide sequence being attached at the A7 alpha amino group and the other said peptide sequence being attached at the A7 epsilon amino group.

3. A peptide according to claim 1, wherein A7 is lysine.

4. A peptide according to claim 1, wherein at least one of the amino acid residues at positions 8, 12, 16, 21, or 27 is replaced by L-leucine.

5. A peptide according to claim 4, wherein XCT is a human, salmon, eel or avian calcitonin amino acid sequence.

6. A peptide according to claim 1 selected from the group consisting of ((Leu-Ala-Ala-Ser-Leu-Ser-Thr-)$_2$-Lys$^7$)cCT; ((Leu-Ala-Gly-Asn-Leu-Ser-Thr)$_2$-Lys-7)xCT (7- 32); ((Leu-Ala-Ser-Asn-Leu-Ser-Thr)$_2$-Lys-7)-xCT (7-32); ((N-acetyl-aminooctanoly-Ser-Thr)$_2$-Lys-7)-xCT (7-32); ((Ser-Thr)$_2$-Lys-7)-xCT (7-32); and ((Chx-Ser-Thr)$_2$-Lys$^7$)-xCT.

7. A peptide according to claim 1 selected from the group consisting of ((Leu-Ala-Ala-Ser-Leu-Ser-Thr)$_2$-Lys-7, Leu-8-cCT(8-32); ((Leu-Ala-Gly-Asn-Leu-Ser-Thr)$_2$-Lys-7, Leu-8) xCT(8-32); ((Leu-Ala-Ser-Asn-Leu-Ser-Thr)$_2$-Lys-7, Leu-8) -hCT(8-32); ((Leu-Ala-Ser-Asn-Leu-Ser-Thr)$_2$-Lys-7, Leu-8,12) -hCT(8-32); ((Leu-Ala-Ser-Asn-Leu-Ser-Thr)$_2$-Lys-7, Leu-8,12,16)hCT(8-32); and ((Chx-Ser-Thr)$_2$-Lys-7, Leu-8) -xCT.

8. A pharmaceutical composition comprising an effective blood calcium-reducing amount of a peptide having the structure set forth in claim 1 in combination with a pharmaceutically acceptable carrier.

9. A method of treating disease by reducing serum calcium levels in a mammal, comprising to said mammal in need of such treatment an effective, blood calcium-reducing amount of a calcitonin peptide analogue having the structure set forth in any one of claims 1, 2, 3, 4, 5, 6 and 7.

10. A method of treating Paget's disease or osteoporosis, comprising:
administering to an affected subject a bone resorption-opposing amount of a synthetic calcitonin having the structure set forth in any one of claims 1, 2, 3, 4, 5, 6 and 7 for a period sufficient to reduce or eliminate the resorption of bone.

11. A hypocalcemic peptide of the formula

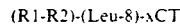

wherein
xCT is a murine, salmon, eel, avian, porcine, bovine, ovine, or human calcitonin sequence;
R1 is H; H—(CH$_2$)$_n$—CO—; H2N—(CH2) n- —CO—; or X—CO—(CH2)n—CO—(wherein X is HO—, cholesterol, adamantyl alcohol (ADA), benzyl alcohol or other aromatic alcohol); L-threonine; D-threonine; L-alanine; D-alanine; L-leucine; D-leucine; cyclopropane carboxyl (CPRC); cyclopentane carboxyl (CPC) cyclohexane carboxyl (CHC); cyclohexylpropionyl (CHX); cyclohexane carboxyl (CHC); cyclohexylpropionyl (CHX); cycloheptane carboxyl (CHPT); adamantaneacetyl (ADM); adamantane carboxyl (ADC); or acyl groups of aromatic or heterocyclic carboxylic acids;
R2 is 1-amino-1-cyclopropane carboxyl (ACPR); 1-amino-1-cyclopentane carboxyl (ACPC); 1-amino-;1-cyclohexane carboxyl (ACHC); 1-amino-1-cycloheptane carboxyl (ACHP); no moiety; or is the same as R1; and pharmaceutically acceptable salts thereof.

12. A pharmaceutical composition comprising an effective blood calcium-reducing amount of a peptide having the structure set forth in claim 11 in connection with a pharmaceutically acceptable carrier.

13. A method of treating disease by reducing serum calcium levels in a mammal, comprising:
selecting a mammal suffering from Paget's disease, osteoporosis, or hypercalcemia of malignancy; and
administering to said mammal an effective, blood calcium-reducing amount of a synthetic calcitonin peptide having the structure set forth in claim 11.

* * * * *

UNITED STATES PATENT AND TRADEMARK OFFICE
CERTIFICATE OF CORRECTION

PATENT NO. : 5,175,146
DATED : December 29, 1992
INVENTOR(S) : Basava, et. al.

It is certified that error appears in the above-indentified patent and that said Letters Patent is hereby corrected as shown below:

Column 38, Line 21, please change "armomatic" to --aromatic--.

Column 38, Line 61, please change "R1-R2-A1-A3-A4-Ser-thr attched" to --R1-R2-A1-A2-A3-A4-Ser-Thr attached--.

Column 39, Line 4, please change "XCT" to --xCT--.

Column 39, Line 12, please change "aminooctanoly" to --aminooctanol--.

Column 39, Line 11, please change "7)xCT" to --7)-xCT--.

Column 39, Line 18, please change "Leu-8) xCT(8-32)" to --Leu-8)-xCT(8-32)--.

Column 39, Line 23, please change "16)hCT)" to --16)-hCT--.

Column 40, Line 25, please change "1-amino-; 1-cyclohexane" to --1-amino-1-cyclohexane--.

Signed and Sealed this

Eleventh Day of January, 1994

Attest:

BRUCE LEHMAN

Attesting Officer

Commissioner of Patents and Trademarks